United States Patent [19]

Takago et al.

[11] Patent Number: 4,730,073

[45] Date of Patent: Mar. 8, 1988

[54] NOVEL ORGANOSILICON COMPOUND AND METHOD FOR THE PREPARATION THEREOF

[75] Inventors: Toshio Takago, Annaka; Yasushi Yamamoto, Takasaki; Goichi Yamaguchi, Urawa; Akira Kurashima, Aizuwakamatsu, all of Japan

[73] Assignee: Shin-Etsu Chemical Co., Ltd., Tokyo, Japan

[21] Appl. No.: 73,469

[22] Filed: Jul. 15, 1987

[30] Foreign Application Priority Data

Jul. 18, 1986 [JP]  Japan .................................. 61-169548

[51] Int. Cl.$^4$ ................................................. C07F 7/10
[52] U.S. Cl. ...................................................... 556/414
[58] Field of Search ........................................ 556/414

[56] References Cited

U.S. PATENT DOCUMENTS 3,113,146  12/1963  Fielding et al. ................. 556/414 X
4,369,300  1/1983  Carter et al. ..................... 556/414 X

*Primary Examiner*—Paul F. Shaver
*Attorney, Agent, or Firm*—Hopgood, Calimafde, Kalil, Blaustein & Judlowe

[57] ABSTRACT

A novel organosilicon compound is disclosed which is an isocyanato group-containing organosilane compound having one or two isopropenyloxy groups as represented by the general formula $(CH_2=CCH_3-O)_n(CH_3)_{3-n}Si(CH_2)_3NCO$, in which n is 1 or 2. The compound can be prepared by heating a mixture of a chlorosilane of the formula $(Cl)_n(CH_3)_{3-n}Si(CH_2)_3NCO$ and acetone in the presence of a tertiary amine compound, e.g., triethyl amine, acting as an acceptor of hydrogen chloride and as a catalyst to effect the enolation reaction.

7 Claims, No Drawings

NOVEL ORGANOSILICON COMPOUND AND METHOD FOR THE PREPARATION THEREOF

BACKGROUND OF THE INVENTION

The present invention relates to a novel class of organosilicon compounds not known in the prior art or not described in any publications as well as a method for the preparation of such novel compounds. More particularly, the invention relates to a novel isocyanato group-containing organosilane compound having a silylenol ether linkage which is a useful compound as a polyisocyanate starting material for the synthetic preparation of urethane compounds and polyurethanes, coupling agent for polyester films and glass fibers used for reinforcement of thermoplastic resins, resinous coating agent and starting material for the preparation of agricultural chemicals and various kinds of silyl group-containing organosilicon compounds as well as a method for the preparation of such a novel compound.

Organosilicon compounds having a silylenol ether linkage in the molecule are known in the prior art and several methods have been proposed for the preparation thereof. For example, Journal of Organic Chemistry, volume 34, page 2324 (1969) and Journal of the American Chemical Society, volume 90, page 4462 (1968) teach a method in which an organosilicon chloride and a carbonyl compound, such as ketones and aldehydes, are reacted.

The organosilicon chloride used in the above proposed method, however, is limited to a simple trialkyl chlorosilane such as trimethyl chlorosilane and tert-butyl dimethyl chlorosilane. No prior art method is known therefore in which the organosilicon compound as the reaction product has an isocyanato group.

SUMMARY OF THE INVENTION

The present invention accordingly provides a class of novel organosilicon compounds not described in any prior art literatures as well as a method for the preparation of such novel compounds.

The organosilicon compound provided by the present invention is an organosilane compound represented by the general formula

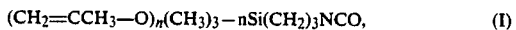

$$(CH_2=CCH_3-O)_n(CH_3)_{3-n}Si(CH_2)_3NCO, \quad (I)$$

in which n is 1 or 2.

The inventive compounds therefore include 3-(isopropenyloxy dimethyl silyl)propyl isocyanate of the formula

$$(CH_2=CCH_3-O)(CH_3)_2Si(CH_2)_3NCO$$

and 3-(diisopropenyloxy methyl silyl)propyl isocyanate of the formula

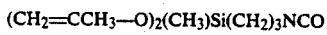

$$(CH_2=CCH_3-O)_2(CH_3)Si(CH_2)_3NCO$$

corresponding to the value of n of 1 and 2, respectively.

The orgnosilicon compound of the above given general formula (I) can be prepared by the reaction of an isocyanato group-containing organosilicon chloride represented by the general formula

$$(Cl)_n(CH_3)_{3-n}Si(CH_2)_3NCO, \quad (II)$$

in which n has the same meaning as defined above, and acetone in the presence of a tertiary amine compound.

DETAILED DESCRIPTION OF THE PREFERRED EMBODIMENTS

The above described reaction between an isocyanato group-containing organosilicon chloride and a carbonyl compound, e.g., acetone, is usually subject to several side reactions such as cyclic dimerization and trimerization due to the isocyanato group having strong activity. The inventors have conducted extensive investigations to suppress such side reactions in the reaction and discovered that the desired organosilicon compound can be obtained in a high yield with little influences by the side reactions when the reaction is performed in the presence of a tertiary amine compound.

One of the starting reactants in the reaction of the inventive method is an isocyanato group-containing organosilicon chloride of the general formula (II) exemplified by 3-(methyl dichlorosilyl)propyl isocyanate and 3-(dimethyl chlorosilyl)propyl isocyanate corresponding to the value of n equal to 2 and 1, respectively. The other reactant to be reacted with the isocyanato group-containing organosilicon chloride is acetone, which is used in an excess amount over stoichiometry in the range from 3 to 15 times of chemical equivalency relative to the isocyanato group-containing organosilicon chloride. In other words, the amount of acetone should be 3 to 15 moles per mole of the chlorine atoms in the isocyanato group-containing organosilicon chloride. The tertiary amine compound added to the reaction mixture should have a sufficiently strong basicity to enolate acetone. Exemplary of suitable tertiary amine compound are triethyl amine, tributyl amine, N-methyl morpholine, diazabicycloundecene and the like. The amount of the tertiary amine compound added to the reaction mixture should be sufficient to neutralize the hydrogen chloride formed by the reaction and further to act as a catalyst to promote the enolation reaction of acetone. It is usually preferable to use the tertiary amine compound in an amount in the range from 2 to 10 moles per mole of the hydrogen chloride to be produced by the reaction. In other words, the amount of the tertiary amine compound should be at least two moles per mole of the chlorine atoms in the isocyanato group-containing organosilicon chloride. When the amount is too small, the velocity of the reaction may be disadvantageously decreased.

The reaction of the inventive method can be performed by heating the reaction mixture formed by mixing the above described reactants and catalyst under reflux or in the range from room temperature to 100° C. or, preferably, from 50 to 70° C. It is optional that the reaction mixture is diluted with an organic solvent such as tetrahydrofuran, dioxane, 1,2-dimethoxy ethane, benzene, toluene and the like having no reactivity with the reactants. Though dependent on various reaction conditions, the reaction is usually complete within about 2 to 5 hours. After completion of the reaction, the reaction mixture is freed from the hydrochloride of the tertiary amine compound precipitated therein by filtration, washing with water or other suitable means followed by distillation to isolate the desired orgnosilicon compound as the reaction product.

The organosilicon compound of the present invention represented by the general formula (I) is, as is mentioned before, a novel compound and useful in various applications, for example, as a polyisocyanate starting material for the synthetic preparation of urethane compounds and polyurethanes, coupling agent for polyester films and glass fibers used for reinforcement of thermoplastic resins, resinous coating agent and starting material for the preparation of agricultural chemicals and various kinds of silyl group-containing organosilicon compounds.

In the following, the organosilicon compound of the invention and the method for the preparation thereof are described in more detail by way of examples.

EXAMPLE 1

Into a flask containing a mixture of 50 g of triethyl amine and 125 ml of acetone kept at 20° to 25° C. were added dropwise 25 g of 3-(methyl dichlorosilyl)propyl isocyanate to form a reaction mixture which was heated at 50° to 60° C. for 2.5 hours to effect the reaction. After completion of the reaction, the reaction mixture was diluted by adding 175 ml of hexane, washed successively and quickly with a cold aqueous solution of sodium hydrogencarbonate, cold 1.5N hydrochloric acid and again cold aqueous solution of sodium hydrogencarbonate followed by dehydration and distilled under reduced pressure to give 6.5 g of a fraction boiling at 87° to 88° C. under a pressure of 4 mmHg after recovery of hexane.

This product was analyzed by the elementary analysis and infrared absorption spectrophotometry to give the results shown below leading to a conclusion that this compound could be identified to be 3-(diisopropenyloxy methyl silyl)propyl isocyanate of the formula $$(CH_2=CCH_3-O)_2CH_3Si(CH_2)_3NCO.$$

Elementary analysis

|  | C, % | H, % | Si, % | N, % |
|---|---|---|---|---|
| Calculated as $C_{11}H_{19}NO_3Si$ | 54.8 | 7.9 | 11.6 | 5.8 |
| Found | 54.3 | 7.1 | 11.3 | 5.7 |

Infrared absorption spectrum
 $2280\ cm^{-1}$: —NCO
 $1650\ cm^{-1}$: —Si—O—CCH$_3$=CH$_2$
 $1060\ cm^{-1}$: —O—Si—CH$_2$—$_3$

EXAMPLE 2

Into a flask containing a mixture of 9.7 g of triethyl amine and 50 ml of acetone kept at 20° to 25° C. were added dropwise 8.5 g of 3-(dimethyl chlorosilyl)propyl isocyanate to form a reaction mixture which was heated at 50° to 60° C. for 3 hours to effect the reaction. After completion of the reaction, the reaction mixture was diluted by adding 70 ml of pentane, washed successively and quickly with a cold aqueous solution of sodium hydrogencarbonate, cold 1.5N hydrochloric acid and again cold aqueous solution of sodium hydrogencarbonate followed by dehydration and distilled under reduced pressure to give 2.3 g of a fraction boiling at 60° to 65° C. under a pressure of 6 mmHg after recovery of pentane.

This product was analyzed by the elementary analysis and infrared absorption spectrophotometry to give the results shown below leading to a conclusion that this compound could be identified to be 3-(isopropenyloxy dimethyl silyl)propyl isocyanate of the formula $$(CH_2=CCH_3-O)(CH_3)_2Si(CH_2)_3NCO.$$

Elementary analysis

|  | C, % | H, % | Si, % | N, % |
|---|---|---|---|---|
| Calculated as $C_9H_{17}NO_2Si$ | 54.2 | 8.6 | 14.1 | 7.0 |
| Found | 54.5 | 8.2 | 14.3 | 6.8 |

Infrared absorption spectrum
 $2280\ cm^{-1}$: —NCO
 $1650\ cm^{-1}$: —Si—O—CCH$_3$=CH$_2$
 $1060\ cm^{-1}$: —O—Si—CH$_2$—$_3$

What is claimed is:

1. An organosilicon compound represented by the general formula $$(CH_2=CCH_3-O)_n(CH_3)_{3-n}Si(CH_2)_3NCO.$$

in which n is 1 or 2.

2. The organosilicon compound as claimed in claim 1 wherein n is 1, which is 3-(isopropenyloxy dimethyl silyl)propyl isocyanate expressed by the formula $$(CH_2=CCH_3-O)(CH_3)_2Si(CH_2)_3NCO.$$

3. The organosilicon compound as claimed in claim 1 wherein n is 2, which is 3-(diisopropenyloxy methyl silyl)propyl isocyanate expressed by the formula $$(CH_2=CCH_3-O)_2(CH_3)Si(CH_2)_3NCO.$$

4. A method for the preparation of an organosilicon compound represented by the general formula $$(CH_2=CCH_3-O)_n(CH_3)_{3-n}Si(CH_2)_3NCO.$$

in which n is 1 or 2, which comprises heating a reaction mixture composed of an isocyanato group-containing orgnosilicon chloride represented by the general formula $$(Cl)_n(CH_3)_{3-n}Si(CH_2)_3NCO,$$

in which n has the same meaning as defined above, and acetone in the presence of a tertiary amine compound.

5. The method as claimed in claim 4 wherein the amount of acetone in the reaction mixture is in the range from 3 to 15 moles per mole of chlorine atoms in the isocyanato group-containing organosilicon chloride.

6. The method as claimed in claim 4 wherein the amount of the tertiary amine compound added to the reaction mixture is in the range from 2 to 10 mols per mole of chlorine atoms in the isocyanato group-containing organosilicon chloride.

7. The method as claimed in claim 4 wherein the tertiary amine compound is triethyl amine.

* * * * *